United States Patent

Shankar

[11] Patent Number: 5,856,473
[45] Date of Patent: Jan. 5, 1999

[54] PROCESS FOR PREPARING 1-(4-FLUOROPHENYL)-3(R)-(3(S)-HYDROXY-3-([PHENYL OR 4-FLUOROPHENYL])-PROPYL)-4(S)-(4-HYDROXYPHENYL)-2-AZETIDINONE

[75] Inventor: Bandarpalle B. Shankar, Branchburg, N.J.

[73] Assignee: Schering Corporation, Kenilworth, N.J.

[21] Appl. No.: 742,012

[22] Filed: Oct. 31, 1996

Related U.S. Application Data

[60] Provisional application No. 60/006,182 Nov. 2, 1995.
[51] Int. Cl.[6] .................................................. C07D 205/08
[52] U.S. Cl. .................................................. 540/200
[58] Field of Search ................................ 540/200

[56] References Cited

U.S. PATENT DOCUMENTS 5,631,365  5/1997  Rosenblum ........................ 540/200

FOREIGN PATENT DOCUMENTS

| 0 210 705 | 2/1987 | European Pat. Off. . |
|---|---|---|
| WO93/02048 | 2/1993 | WIPO . |
| PCT/US/07291 | 1/1995 | WIPO . |
| WO95/08532 | 3/1995 | WIPO . |
| WO95/26334 | 10/1995 | WIPO . |

OTHER PUBLICATIONS

Shankar, Tet. Letters 37, 4095 (1996).

Primary Examiner—Mark L. Berch
Attorney, Agent, or Firm—Anita W. Magatti

[57] ABSTRACT

A process for preparing a compound of the formula

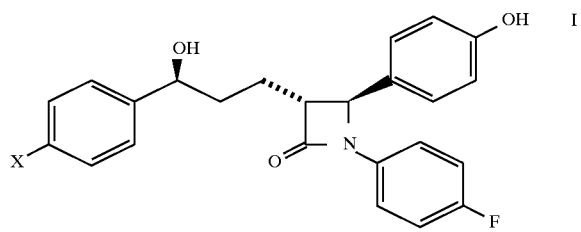

wherein X is H or F, comprising:

(a) alkylation of a 3-unsubstituted chiral azetidinone of the formula

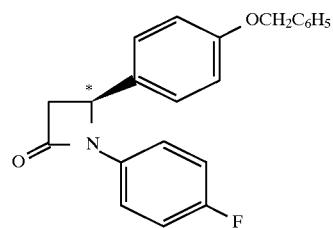

with cinnamyl bromide or 4-fluorocinnamyl bromide;

(b) Wacker oxidation of the product of step (a);

(c) reduction of the ketone product of step (b); and (d) debenzylation of the ketone of step (c).

5 Claims, No Drawings

PROCESS FOR PREPARING 1-(4-FLUOROPHENYL)-3(R)-(3(S)-HYDROXY-3-([PHENYL OR 4-FLUOROPHENYL])-PROPYL)-4(S)-(4-HYDROXYPHENYL)-2-AZETIDINONE

This application claims benefit of USC Provisional Appln. No. 60/006,182 filed Nov. 2, 1995.

BACKGROUND

This invention relates to a process for preparing 1-(4-fluorophenyl)-3(R)-(3(S)-hydroxy-3-(4-fluorophenyl) propyl)-4(S)-(4 -hydroxyphenyl)-2-azetidinone and 1-(4-fluorophenyl)-3(R)-(3(S)-hydroxy-3-phenylpropyl)-4(S)-(4-hydroxyphenyl)-2-azetidinone, compounds useful as hypocholesterolemic agents, and to the preparation of 1-(4-fluorophenyl)-3(R)-(3-(4-fluorophenyl)-3-oxopropyl)-4(S)-(4-benzyloxyphenyl)-2-azetidinone and 1-(4-fluorophenyl)-3(R)-(3-phenyl-3-oxopropyl)-4(S)-(4-benzyloxyphenyl)-2-azetidinone, intermediates in that process.

WO 95/08532 discloses a genus of hypocholesterolemic agents comprising the 3-hydroxypropyl-substituted azetidinones named above and describes several processes suitable for preparing said azetidinones. WO 93/02048 discloses stereoselective processes for producing azetidinones comprising cyclizing intermediates which include the 3-position and 4-position substituents desired in the final product. PCT/US94/07291 discloses a modification of the processes disclosed in WO 93/02048 wherein the β-aminoamides are cyclized by reating with a silylating agent and a fluoride ion catalyst. WO95/26334 discloses chiral β-amino esters, a process for preparing them, and a process for cyclizing a chiral β-amino ester to obtain a chiral 3-unsubstituted azetidinone. The PCT publications and application are related, respectively, to U.S. Ser. Nos. 08/257,593 (filed Jun. 9, 1994), 08/178,312 (filed Jan. 11, 1994), 08/089,357 (filed Jul. 9, 1993) and 08/403,081 (filed Mar. 13, 1995), all incorporated herein by reference.

SUMMARY OF THE INVENTION

This invention provides a chiral process for preparing a compound having the structural formula I:

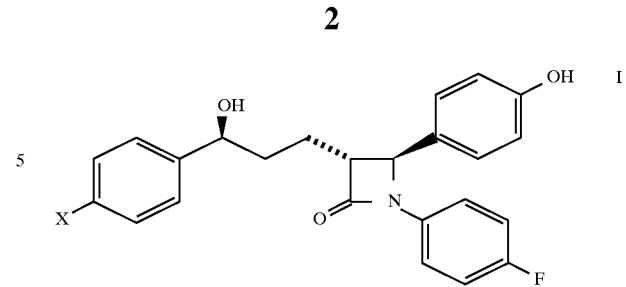

wherein X is H or F, comprising:

(a) alkylating a chiral 3-unsubstituted azetidinone of formula II with cinnamyl bromide or 4-fluorocinnamyl bromide, III, to obtain a propenyl derivative of formula IV:

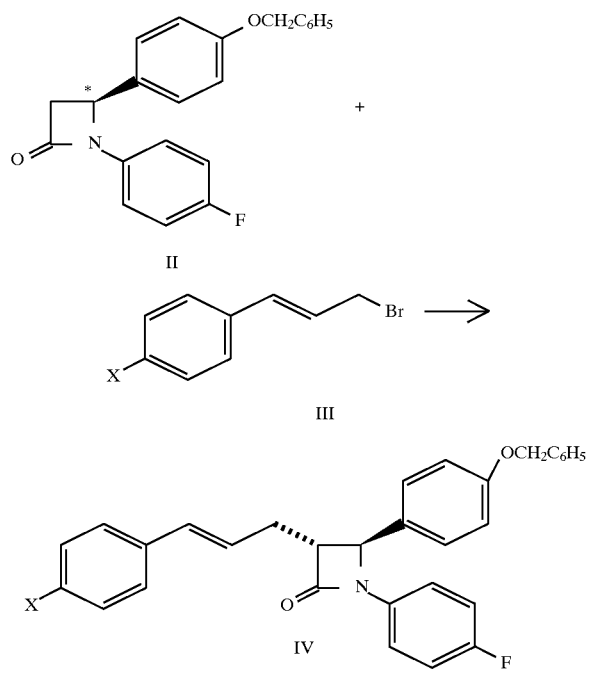

(b) oxidizing a compound of formula IV to obtain a corresponding ketone of formula V:

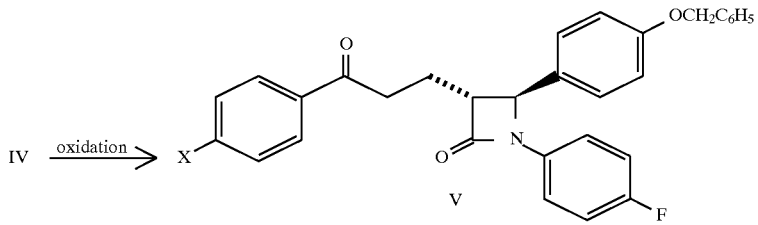

(c) reducing a ketone of formula V to a hydroxy compound of formula VI:

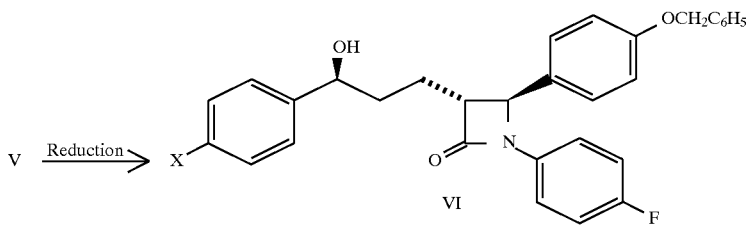

(d) removing the benzyl protecting group from a compound of formula VI to obtain a compound of formula I.

The invention also relates in particular to step (b), wherein the propenyl intermediate, IV, is oxidized to the ketone, V.

The process of this invention, compared to the procedure for preparing the compounds of formula I disclosed in WO 95/08532, is a simpler procedure, involving fewer steps and milder reagents, and having an improved yield. The ketone intermediate is produced more efficiently and from a more accessible precursor. The Wacker oxidation step proceeds in a regioselective manner to provide the benzylic oxidation product.

DETAILED DESCRIPTION

In step (a) of the claimed process, the chiral 3-unsubstituted azetidinone of formula II is alkylated with cinnamyl bromide or 4-fluoro-cinnamyl bromide (III) by the method described in WO95/26334, i.e., in an inert anhydrous solvent such as tetrahydrofuran (THF) in the presence of a strong base such as lithium diisopropyl amine (LDA) at a low temperature of about −70° to −78° C., to obtain a propenyl compound of formula IV.

In step (b), the modified Wacker oxidation comprises treating a propenyl compound of formula IV with an oxidant such as benzoquinone, a catalyst such as palladium acetate, and a catalytic amount of perchloric acid in a solvent such as acetonitrile:water or dimethylformamide:water at a temperature range of 25° −50° C., preferably about 25° C., for 3–12 hours, preferably for about 6 hours. The oxidation product is purified by conventional methods, typically by silica gel chromatography, to obtain the compound of formula V in approximately a 70% yield. Alternatively, standard Wacker oxidation conditions can be used, i.e., palladium chloride and cupric chloride under an oxygen atmosphere.

In step (c), the ketone intermediate of formula V is reduced to the corresponding hydroxy compound, VI, under conditions well known in the art, for example by using a reagent such as $NaBH_3$ in the presence of a chiral promoting agent such as a chiral borane (e.g., (R)-tetrahydro-1-methyl-3,3-diphenyl-1H,3H-pyrolo-[1,2-c][1,3,2]oxazaborole).

In step (d), the benzyl protecting group on the compound of formula VI is removed by well known methods, for example by hydrogenating an alcoholic solution, e.g., an ethanolic solution, of the compound of formula VI with Pd/C under $H_2$ at reduced pressure.

The chiral 3-unsubstituted azetidinone starting material of formula II is made by cyclization of a chiral β-amino ester according to the process described in WO95/26334 or the corresponding U.S. application, incorporated herein by reference.

The propenyl compound of formula IV can also be prepared by the process exemplified by the following reaction scheme:

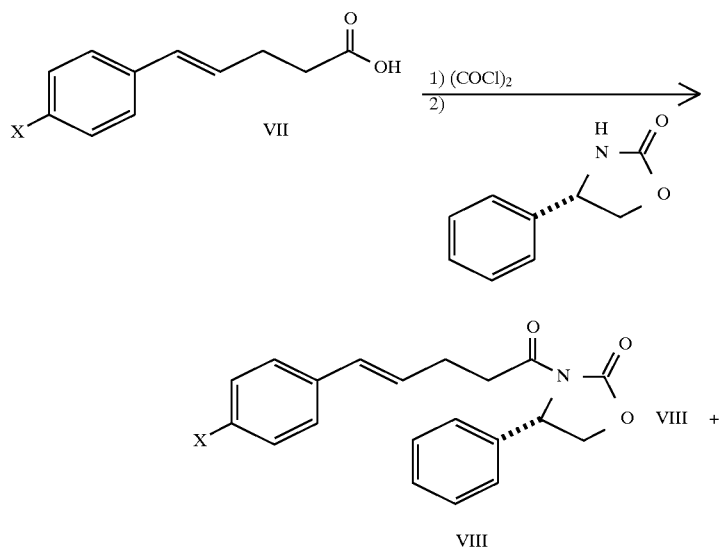

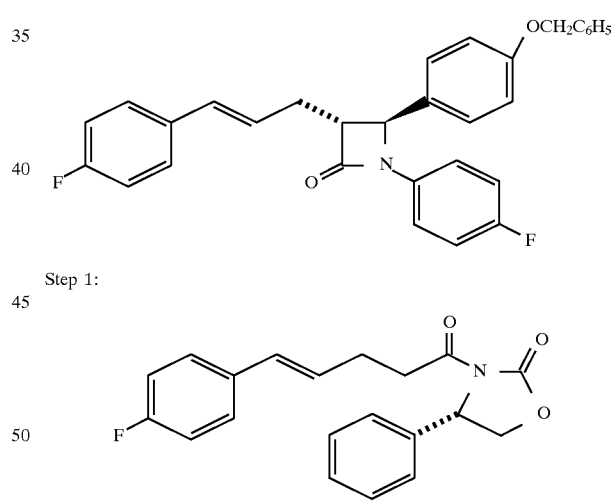

wherein fluorophenyl pentenoic acid, VII, is converted to the corresponding acid chloride and reacted with a chiral auxiliary such as (S)-(+)-4-phenyl-2-oxazolidine. The product, VIII, is enolized and condensed with an imine of formula IX, and the product of that reaction, X, is cyclized by treatment with a silylating agent such as bis trimethylsilylacetamide (BSA) followed by a fluoride ion catalyst such as tetrabutyl ammonium fluoride (TBAF).

Following are examples of the claimed process.

Example 1

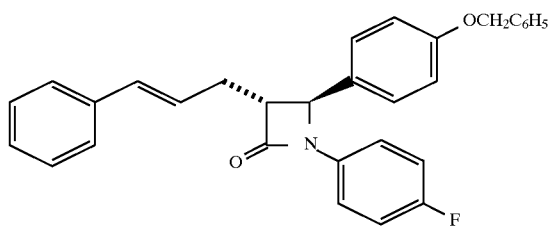

Cool a solution of 1-(4-fluorophenyl)-4(S)-(4-benzyloxyphenyl)-2-azetidinone (2.5 g, 0.007 mole) in THF (30 mL) to −78° C., add freshly prepared LDA (0.0084 mole) in THF (10 mL) and stir for 1 h at −78° C. Add cinnamyl bromide (1.68 g, 0.0084 mole) dropwise as a THF solution (5 mL). Allow the mixture to warm to −20° C. over 4 h and quench with aqueous NH$_4$Cl (20 mL). Extract the product into ether (50 mL), wash with water (2×30 mL) and brine (1×30 mL), dry over MgSO$_4$, filter and concentrate. Purify the resultant crude mixture by flash chromatography on silica gel, eluting with 30% EtOAc/hexanes to obtain 0.268 g (70%) of the title compound plus 0.04 g of the cis isomer. H$^1$NMR: (300 MHz, CDCl$_3$): δ 2.7 (m, 1H), 2.9 (m, 1H), 4.68 (d, J=2 Hz), 5.05 (s, 2H), 6.26 (m, 1H), 6.5 (d, J=12 Hz, 1H), 6.9–7.5 (m, 18H).

Example 2

Step 1:

Slowly add oxalyl chloride (2.2 g) and DMF (2 drops) to a solution of fluorophenyl pentenoic acid (2.41 g) in CH$_2$Cl$_2$ (30 mL) at 0° C., warm the mixture to room temperature and reflux for 1 h. Evaporate the solvent under reduced pressure and azeotrope off the excess oxalyl chloride with CH$_2$Cl$_2$ (2×50 mL). Redissolve the resultant acid chloride in CH$_2$Cl$_2$ (20 mL) and add the solution dropwise to a cooled solution of (S)-(+)-4-phenyl-2-oxazolidone (1.82 g), N,N-diisopropylethylamine (DIPEA) (3.2 g) and N-dimethylaminopyridine (0.056 g) in CH$_2$Cl$_2$ (30 mL). Stir the resulting mixture for 10 h, then dilute with CH$_2$Cl$_2$ (150 mL). Wash the organic layer with 0.5N HCl (2×50 mL), water (1×50 mL) and brine (1×50 mL), then dry and concentrate to crystallize the desired product. Recrystallize from ethyl acetate (EtOAc)/hexane and collect the product by filtration to obtain 3.8 g (95%). $^1$H NMR: (300 MHz, CDCl$_3$): δ 2.5 (m, 2H), 3.1 (m, 2H), 4.25 (dd, J=8, 3 Hz, 1H), 4.68 (dd, appt. t, J=8 Hz), 5.45 (dd, J=8, 3 Hz, 1H), 6.1 (m, 1H), 6.35 (d, J=12 Hz, 1H), 6.9–7.5 (m, 9H).

Step 2:

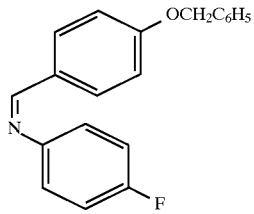

Stir a mixture of benzyloxybenzaldehyde (2.12 g, 0.01 mole) and fluoroaniline (1.11 g, 0.01 mole) in isopropanol (25 mL) overnight. Filter to collect the product and dry overnight to obtain 2.8 g.

Step 3:

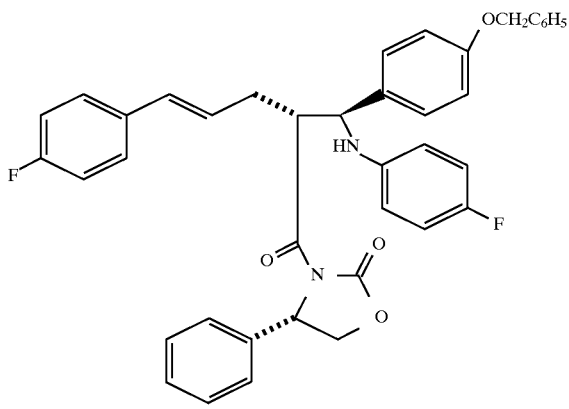

To a solution of the product of step 1 (1.3 g) in CH$_2$Cl$_2$ (20 mL) at −20° to −25° C., slowly add a 1M solution of TiCl$_4$ in CH$_2$Cl$_2$ (3.8 mL) and stir at −20° C. for 10 min. Slowly add DIPEA (1.3 mL) and stir for 30 min. at −20° C. Add the product of step 2 (2.34 g) in CH$_2$Cl$_2$ (20 mL) and stir for 1 h at a temperature below −20° C. Quench the reaction by adding glacial acetic acid (1.3 mL) in CH$_2$Cl$_2$ (3 mL) and stir for 30 min. Pour the mixture into aqueous 2N H$_2$SO$_4$ (30 mL), stir for 30 min. and add EtOAc (100 mL). Wash the organic layer with saturated aqueous NaHCO$_3$ and brine, concentrate and recrystallize from EtOAc/hexane to obtain 1.68 g of the desired product (67%). $^1$H NMR: (300 MHz, CDCl$_3$): δ 2.35 (m, 1H), 2.6 (m, 1H), 4.15 (m, 1H), 4.5 (m, 1H), 4.7 (m, 1H), 5.0 (s, 2H), 5.15 (s, 2H), 5.4 (m, 1H), 6.0 (m, 1H), 6.3 (d, J=12 Hz, 1H), 6.5 (br s, 1H), 6.7–7.9 (m, 22H).

Step 4:

To a suspension of the product of step 3 (1.0 g) in toluene (15 mL) at 60° C., add BSA (1 mL) and heat to 80° C. After 2 h, cool the reaction mixture to 50° C., add TBAF (0.028 g), stir for 2 h more, cool and dilute with EtOAc (100 mL). Wash the organic layer with 0.5N HCl (2×50 mL), water (1×50 mL) and brine (1×50 mL), dry, filter and concentrate. Purify the crude product by passing through a short pad of silica gel, eluting with 10% EtOAc/hexane to obtain 0.68 g of the title compound (90%). $^1$H NMR: (300 MHz, CDCl$_3$): δ 2.7 (m, 1H), 2.85 (m, 1H), 3.25 (m, 1H), 4.68 (d, J=2Hz, 1H), 5.05 (s, 2H), 6.15 (m, 1H), 6.45 (d, J=12 Hz, 1H), 6.9–7.5 (m, 17H).

Example 3

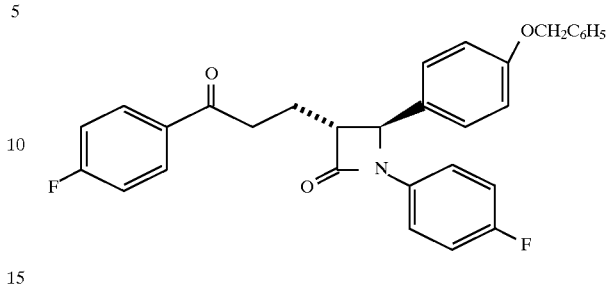

Combine the product of Example 2 (4.6 mmol), Pd(OAc)$_2$ (0.0028 g, 2 mol %), benzoquinone (0.07 g, 1.5 eq.) and perchloric acid (catalytic; 0.008 mL) in acetonitrile:water (7:1) (8 mL) and stir for 6 h. Dilute the reaction mixture with EtOAc (50 mL) and wash with water (4×25 mL). Dry the organic layer over MgSO$_4$, filter and treat the filtrate with charcoal (4 g) to remove the palladium catalyst, then filter off the charcoal and concentrate the filtrate. Purify the resultant residue by silica gel preparative plate chromatography, eluting with 30% EtOAc/hexane to obtain the product of step 1 in 70–80% yield. H$^1$NMR: (300 MHz, CDCl$_3$): δ 2.34 (m, 2H), 3.15 (m, 2H), 3.3 (m, 1H), 4.69 (d, J=1.6 Hz, 1H), 5.05 (s, 2H), 6.8–7.5 (m, 15H), 8.00 (m, 2H).

Example 4

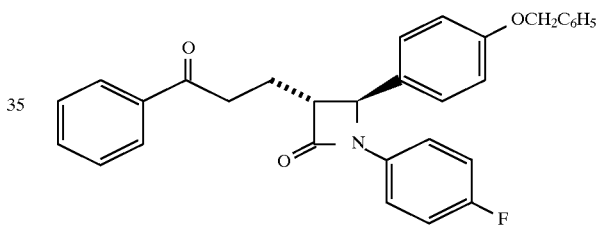

Using the procedure of Example 3, oxidize the azetidinone of Example 1 to obtain the title compound. H$^1$NMR: (300 MHz, CDCl$_3$): δ 2.34 (m, 2H), 3.16 (m, 2H), 3.25 (m, 1H), 4.68 (d, J=2 Hz, 1H), 5.04 (s, 2H), 6.9–7.6 (m, 16H), 7.95 (d, 7 Hz,, 2H).

Example 5

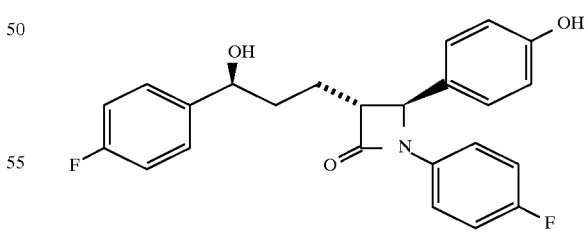

Step 1: Add (R)-tetrahydro-1-methyl-3,3-diphenyl-1H, 3H-pyrrolo[1,2-c]-[1,3,2]oxazaborole (120 mg, 0.43 mmol) to 1-(4-fluorophenyl)-3(R)-(3-(4-fluorophenyl)-3-oxopropyl)-4(S)-(4-benzyloxyphenyl)-2-azetidinone (0.95 g, 1.91 mmol) in THF (3 mL) and cool to −20° C. After 5 min., add borohydride-dimethylsulfide complex (2M in THF, 0.85 mL, 1.7 mmol) dropwise over 0.5 h. After a total of 1.5 h, add CH$_3$OH followed by HCl (1N) and extract the reaction mixture with EtOAc to obtain 1-(4-fluorophenyl)-3(R)-(3(S)-(4-fluorophenyl)-3-hydroxypropyl)-4(S)-(4-benzyloxyphenyl)-2-azetidinone.

Step 2: Add 10% Pd/C (0.03 g) to a solution of the product of step 1 (0.4 g, 0.8 mmol) in ethanol (2 mL) and stir under a pressure of H₂ gas (60 psi) for 16 h. Filter the reaction mixture and concentrate to obtain the title compound.

I claim:

1. A process for preparing a compound of the formula

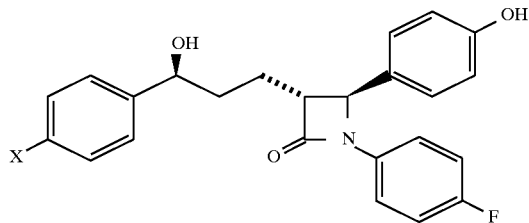

wherein X is H or F, comprising (a) alkylation of the 3-unsubstituted azetidinone of the formula

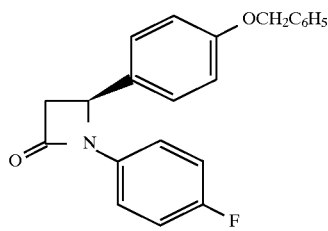

with cinnamyl bromide or 4-fluorocinnamyl bromide to obtain a compound of the formula

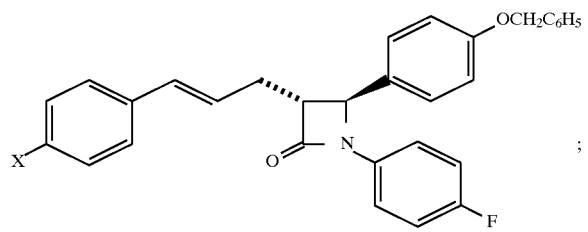

(b) oxidation of the product of step (a) to obtain a compound of the formula

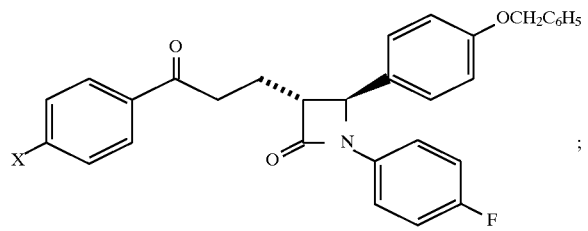

(c) reduction of the ketone of step (b) to obtain a compound of the formula

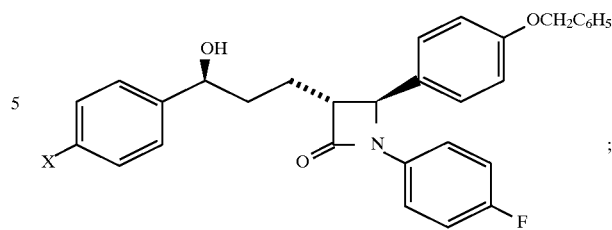

(d) debenzylation of the product of step (c).

2. A process of claim 1 comprising:

(a) alkylating 1-(4-fluorophenyl)-4(S)-(4-benzyloxyphenyl)-2-azetidinone with cinnamyl bromide or 4-fluorocinnamyl bromide in the presence of a strong base;

(b) oxidizing the product of step (a) with benzoquinone and palladium acetate in the presence of a catalytic amount of perchloric acid;

(c) reducing the ketone of step (b) in the presence of a chiral borane reducing agent; and (d) debenzylation of the product of step (c) by hydrogenation.

3. A process of claim 2 wherein the strong base of step (a) is lithium diisopropyl amine; the reducing agent of step (c) is NaBH₃ and the chiral promoting agent is (R)-tetrahydro-1-methyl-3,3-diphenyl-1H,3H-pyrrolo[1,2-c]-[1,3,2]oxazaborole; and the debenzylation of step (d) comprises hydrogenation of an alcoholic solution of the product of step (c) with palladium on carbon under H₂ at reduced pressure.

4. A process for preparing a compound of the formula

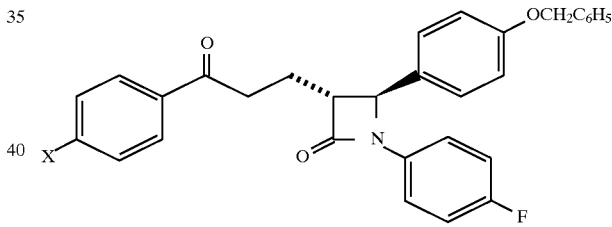

wherein X is H or F, comprising oxidation of a compound of the formula

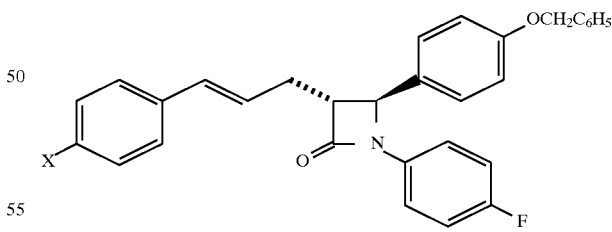

wherein X is H or F.

5. A process of claim 4 comprising oxidation with benzoquinone and palladium acetate in the presence of a catalytic amount of perchloric acid.

* * * * *